US00PP21430P2

(12) United States Plant Patent
Radler

(10) Patent No.: US PP21,430 P2
(45) Date of Patent: Nov. 2, 2010

(54) CLIMBING ROSE PLANT NAMED 'RADCANCAN'

(50) Latin Name: *Rosa hybrida*
Varietal Denomination: Radcancan

(75) Inventor: William J. Radler, Greenfield, WI (US)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 12/588,147

(22) Filed: Oct. 6, 2009

(51) Int. Cl.
*A01H 5/00* (2006.01)

(52) U.S. Cl. ..... Plt./114

(58) Field of Classification Search ..... Plt./114
See application file for complete search history.

*Primary Examiner*—Annette H Para
(74) *Attorney, Agent, or Firm*—Buchanan Ingersoll & Rooney PC

(57) ABSTRACT

A new and distinct variety of rose plant is provided which forms in abundance on a substantially continuous basis attractive semi-double blossoms wherein the coloration is magenta red to light pink suffused with cream-white towards the center. The vegetation is vigorous and the growth habit is upright and climbing. Attractive ornamental medium green foliage having a semi-glossy aspect is formed. During observations to date the disease resistance has been excellent, particularly with respect to blackspot. The cold hardiness of the new variety also is excellent, particularly for a climbing rose. The new variety is particularly well suited for growing as distinctive ornamentation in parks, gardens, and residential settings. Instead of a climber, the plant can alternatively be trimmed and grown as a compact rose bush in the absence of support.

1 Drawing Sheet

Botanical/commercial classification: *Rosa hybrida*/Climbing Rose Plant.

Varietal denomination: cv. Radcancan.

SUMMARY OF THE INVENTION

The new variety of *Rosa hybrida* shrub rose plant of the present invention was created at Greenfield, Wis., U.S.A., by artificial pollination wherein two parents were crossed which previously had been studied in the hope that they would contribute the desired characteristics. The cross was carried out during July 2001. The female parent (i.e., the seed parent) was the 'Radcovery' variety (non-patented in the United States). The male parent (i.e., the pollen parent) of the new variety was the 'Radcotee' variety (non-patented in the United States). The parentage of the new variety can be summarized as follows:

'Radcovery'×'Radcotee'.

The seeds resulting from the above pollination were sown and small plants were obtained which were physically and biologically different from each other. Selective study resulted in the identification of a single plant of the new variety.

It was found that the new climbing rose plant of the present invention possesses the following combination of characteristics:

(a) abundantly and substantially continuously forms attractive semi-double blossoms that are magenta red to light pink suffused with cream-white towards the center,
(b) exhibits an upright and climbing growth habit,
(c) forms vigorous vegetation,
(d) forms attractive ornamental medium green foliage with a semi-glossy aspect,
(e) exhibits excellent resistance to blackspot, and
(f) exhibits excellent cold hardiness for a climbing rose.

The new variety displays a good repeat blooming character. The winter hardiness is above average for a rose of this class. The growth habit is very vigorous and the canes commonly are of medium to heavy caliper for the class.

The new variety well meets the needs of the horticultural industry. It can be grown to advantage as an attractive climber in parks, gardens, public areas, and in residential settings. It alternatively can be trimmed and grown as a compact rose bush in the absence of support. The new variety is particularly well suited for providing attractive ornamentation in the landscape. The blossom coloration contrasts nicely with the semi-glossy medium green foliage.

The new variety of the present invention can be readily distinguished from its ancestors, as well as other climbing rose varieties that are available to others for comparison, such as the 'Radwin' variety (U.S. Plant Pat. No. 19,310) and the 'Radbrite' variety (U.S. Plant Pat. No. 17,391). More specifically, the blossoms of the 'Radwin' variety are entirely red in coloration, and the blossoms of the 'Radbrite' variety are pink with a yellow eye.

The characteristics of the new variety have been found at Wasco, Calif., U.S.A., and near West Grove, Pa., U.S.A., to be homogeneous and stable and to be strictly transmissible by asexual propagation, such as budding, grafting, and the rooting of cuttings, from one generation to another. The new variety reproduces in a true-to-type manner by such asexual propagation.

The new variety has been named 'Radcancan' and is being marketed under the CANCAN trademark.

BRIEF DESCRIPTION OF THE PHOTOGRAPH

The accompanying photograph shows, as nearly true as it is reasonably possible to make the same in a color illustration of this character, a typical specimen of the new variety. A mature flowering plant is shown during July while growing with support in the garden of its originator at Greenfield, Wis., U.S.A. The attractive blossoms, floral buds, and foliage are displayed.

DETAILED DESCRIPTION

The chart used in the identification of colors is that of The Royal Horticultural Society (R.H.S. Colour Chart), London, England. The description is based on the observation of three-year-old specimens of the new variety during July while growing outdoors on their own roots near West Grove, Pa., U.S.A.

Class: Climbing Rose.

Plant:

*Height.*—Approximately 4 to 5 feet on average at the end of the growing season, and commonly assumes a mature height of approximately 8 to 10 feet.

*Width.*—Approximately 3 to 4 feet on average at the end of the growing season, and commonly continues to display approximately the same width at full maturity.

*Habit.*—Upright and climbing.

Branches:

*Color.*—Young stems: Commonly Yellow-Green Group 144B with Greyed-Red Group 178B. Adult wood: Green Group 143C.

*Texture.*—Young stems: Rough with many small thorns. Adult wood: Somewhat rough to the touch.

*Caliper.*—Canes are medium to heavy in caliper.

*Thorns.*—On young wood: commonly range from approximately 2 to 13 mm in length. On mature wood: commonly range from approximately 2 to 9 mm in length.

Leaves:

*Leaflet number.*—3, 5, and 7.

*Leaflet texture.*—On the upper side generally smooth with an indentation towards the mid-vein, and on the under side somewhat rough.

*Leaf size.*—Commonly approximately 4 cm in length on average, and approximately 3 cm in width on average at the widest point.

*Leaflet shape.*—Oval to somewhat ovate with acute to somewhat acuminate apices, and rounded bases.

*Leaflet margins.*—Serrulate.

*Leaflet size.*—Commonly approximately 35 mm in length on average, and approximately 25 mm in width on average at the widest point.

*Overall appearance.*—Abundant, and medium green with a semi-glossy finish.

*Color.*—Young leaves: upper surfaces commonly are Green Group 137B with edges of Greyed-Purple Group 183D, and under surfaces commonly are Green Group 139C. Mature leaves: upper surfaces commonly are Green Group 137A, and under surfaces commonly are Green Group 148B.

*Stipules.*—Yellow-Green Group 144B.

*Petiole.*—Yellow-Green Group 144B blended with Greyed-Red Group 178B.

*Rachis.*—Typical in appearance.

Inflorescence:

*Bearing.*—Commonly in clusters of approximately 4 to 7 blossoms.

*Peduncle.*—Near Yellow-Green Group 146D.

*Sepals.*—Length: commonly approximately 20 mm on average. Width: commonly approximately 5 mm on average. Number: five.

*Buds.*—Shape: commonly ovoid to pointed. Size: medium to small. Length: as the calyx breaks commonly approximately 15 mm on average. Diameter: as the calyx breaks commonly approximately 13 mm on average at the widest point. Texture: smooth. Color (as the calyx breaks): commonly near Greyed-Purple Group 187A towards the tip and Greyed-Purple Group 185A elsewhere.

*Flower.*—Form: semi-double. Configuration: when partially opened high-centered with the petals being somewhat loosely spiraled and the petal edges being somewhat slightly reflexed outwards, and when fully opened somewhat cup-shaped with the petal edges being flat to undulated and very slightly reflexed outward. Diameter: commonly approximately 5 to 7 cm on average when fully open. Color (when opening begins): upper surface: near Red Group 52A at the tips of the petals, and Yellow Group 1C elsewhere. under surface: near Greyed-Purple Group 183A at the tips and mid-line of the petals, and Red Group 53C elsewhere. Color (when blooming): upper surface: Red-Purple Group 57A at the edges of the petals, and Yellow Group 4D elsewhere. Under surface: Red-Purple Group 58A at the edges of the petals, and Yellow-White Group 158A elsewhere. Color (at end of blooming) upper surface: Red-Purple Group 58B to Red-Purple Group 59A at the edges of the petals, and Green-Yellow Group 1C towards the center. under surface: Red-Purple Group 58A at the edges of the petals, and Yellow Group 2D elsewhere. Lastingness: commonly approximately 4 or 5 days or more on the plant depending upon environmental conditions, and approximately 4 to 5 days when cut and placed in a vase. Petal number: commonly approximately 12 to 15 (e.g., 13) on average. Petaloid number: commonly approximately 3 on average per flower. Petal size: commonly approximately 30 mm in length on average and approximately 27 mm in width on average. Petal texture: smooth and velvety on both surfaces. Fragrance: very light sweet rose fragrance. Petal drop: very good, with the petals commonly dropping cleanly and freely. Stamen number: commonly approximately 30 on average. Pollen: commonly is present in a moderate to abundant quantity and commonly is near Yellow Group 13B in coloration. Pistils: commonly approximately 20 on average.

*Receptacle.*—Ovaries commonly are enclosed within the calyx.

Development:

*Vegetation.*—Vigorous.

*Blossoming.*—Very abundant and substantially continuous during the growing season.

*Resistance to diseases.*—Excellent with respect to blackspot and powdery mildew when compared to commercial rose varieties being grown under comparable conditions near West Grove, Pa., U.S.A.

*Cold hardiness.*—Excellent, and has proven to be completely winter hardy in U.S.D.A. Hardiness Zone Nos. 5 to 9.

The new 'Radcancan' variety has not been observed under all possible environmental conditions to date. Accordingly, it is possible that the phenotypic expression may vary somewhat with changes in light intensity and duration, cultural practices, and other environmental conditions.

I claim:

1. A new and distinct climbing rose plant characterized by the following combination of characteristics:

(a) abundantly and substantially continuously forms attractive semi-double blossoms that are magenta red to light pink suffused with cream-white towards the center, (b) exhibits an upright and climbing growth habit, (c) forms vigorous vegetation, (d) forms attractive ornamental medium green foliage with a semi-glossy aspect, (e) exhibits excellent resistance to blackspot, and (f) exhibits excellent cold hardiness for a climbing rose; substantially as herein shown and described.

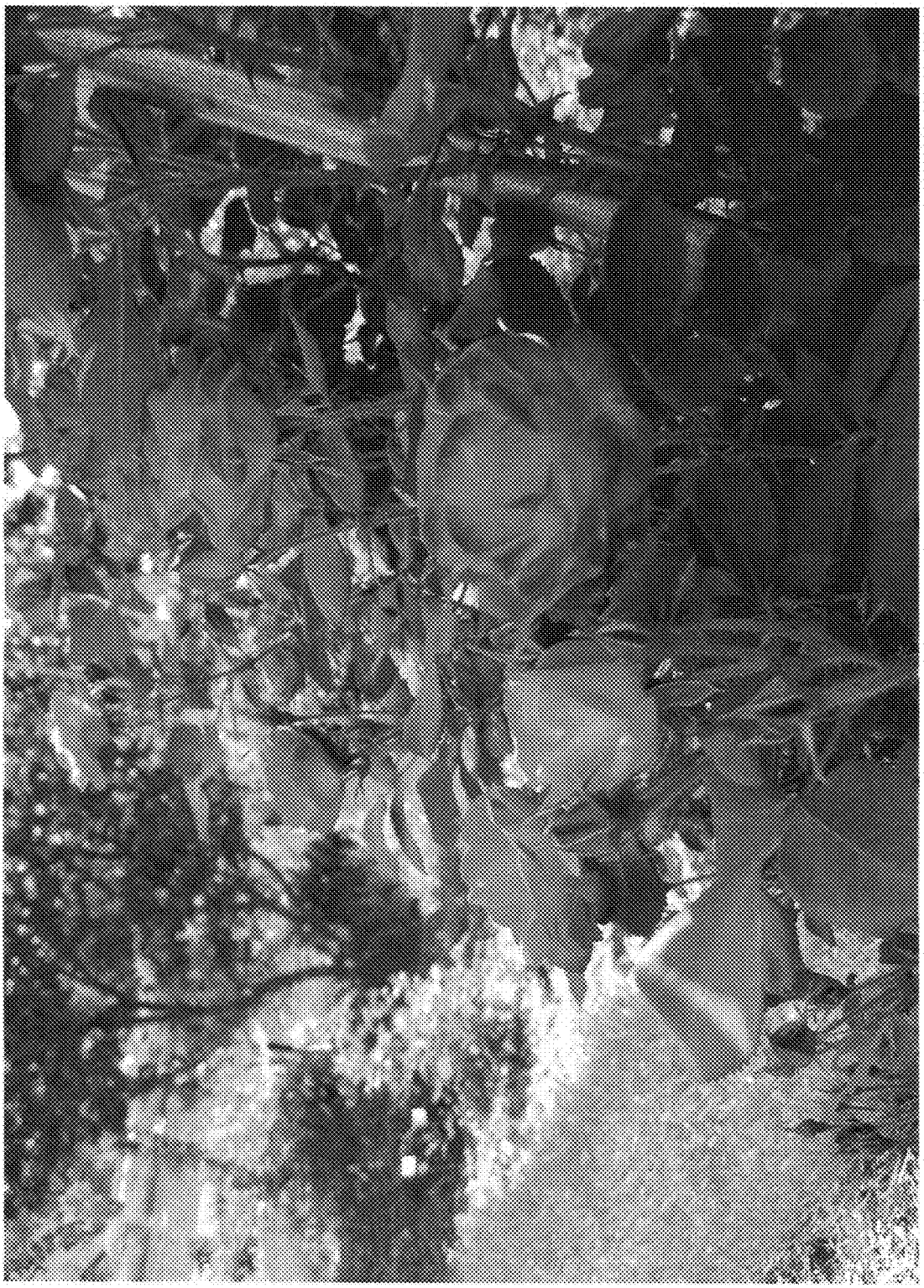

* * * * *